United States Patent [19]
Pero

[11] Patent Number: 6,100,299
[45] Date of Patent: Aug. 8, 2000

[54] N-ACETYL 3-CHLOROPROCAINAMIDE, ACID ADDITION SALTS THEREOF, AND METHODS OF USE

[75] Inventor: Ronald W. Pero, Lund, Sweden

[73] Assignee: OXiGene, Inc., Boston, Mass.

[21] Appl. No.: 09/093,474

[22] Filed: Jun. 8, 1998

Related U.S. Application Data

[63] Continuation-in-part of application No. 08/807,071, Feb. 27, 1997, Pat. No. 6,028,111, which is a continuation-in-part of application No. 08/807,497, Feb. 27, 1997
[60] Provisional application No. 60/013,072, Mar. 8, 1996.
[51] Int. Cl.$^7$ ...................... A61K 31/165; C07C 233/00; C07C 235/00; C07C 237/00
[52] U.S. Cl. ............................................ 514/620; 564/163
[58] Field of Search ............................. 564/163; 514/620

[56] References Cited

PUBLICATIONS

AN 1975:156684, Bundeanu et al. (1974).
AN 1995:870709, Rummel et al. (1995).
AN 1997:38135, Seelig et al. (1996).
AN 1995:663483, Hill et al. (1995).
AN 1990:417472, Robert–Piessard et al, (1990).

*Primary Examiner*—Keith D. MacMillan
*Attorney, Agent, or Firm*—Cooper & Dunham LLP

[57] ABSTRACT

N-acetyl-3-chloroprocainamide, its acid addition salts, mixtures thereof, formulations containing the same for therapeutic administration to a human or other animal, and uses thereof in methods of inhibiting or killing tumor or cancer cells and in methods of treating inflammatory disorders.

9 Claims, 1 Drawing Sheet

N-ACETYL 3-CHLOROPROCAINAMIDE, ACID ADDITION SALTS THEREOF, AND METHODS OF USE

CROSS REFERENCE TO RELATED APPLICATIONS

This application is a continuation-in-part of U.S. patent applications Ser. Nos. 08/807,071 now 6,028,111 and 08/807,497 (in which a divisional continued prosecution application under 37 C.F.R. §1.53(d) was filed Mar. 4, 1998), both of which were filed on Feb. 27, 1997, and both of which claim the right of priority of U.S. provisional patent application No. 60/013,072, filed Mar. 8, 1996. The entire disclosures of both of the aforesaid copending applications are incorporated herein by this reference.

BACKGROUND OF THE INVENTION

This invention relates to a novel N-acetyl substituted aryl analog of an N-substituted benzamide, its acid addition salts, the use thereof as direct chemotherapeutic agents or as sensitizers for radiation and/or other chemotherapeutic agents in methods of inhibiting or killing tumor and cancer cells in human patients or other warm-blooded animals, and also the use thereof as anti-inflammatory agents in methods of treating inflammatory disorders in human patients or other warm-blooded animals.

The invention described in the aforementioned application Ser. No. 08/807,497 ("the '497 application"), in a first aspect, broadly contemplates the provision of a method of inhibiting or killing tumor or cancer cells in a human patient, consisting essentially of treating the patient with a composition selected from the group consisting of aryl N-substituted carboxamides having one or more aryl halo or one or more aromatic nitrogens, acid addition salts of these carboxamides, and mixtures thereof. In this method, the defined carboxamides act directly as chemotherapeutic agents, not merely as sensitizers for radiation and other chemotherapeutic agents. The term "consisting essentially," as used in the definition of the above-described method, excludes the use or presence of radiation or chemotherapeutic agents (other than the stated carboxamides and/or acid addition salts thereof) in the practice of the method.

The invention of the '497 application in a second aspect contemplates the provision of a method of inhibiting or killing tumor or cancer cells in a human patient, consisting essentially of treating the patient with radiation or a chemotherapeutic agent together with a composition selected from the group consisting of N-substituted nicotinamides, N-(2-diethylamino-ethyl)-4-amino-3-chlorobenzamide (hereinafter sometimes referred to as 3-chloroprocainamide or 3-CPA), their acid addition salts, and mixtures thereof, in an amount effective to enhance the cytotoxicity of the radiation or chemotherapeutic agent employed. The selected composition, in the latter method, acts as a sensitizer for the radiation or chemotherapeutic agent. The compositions used as such sensitizers are within the broadly defined class of aryl N-substituted carboxamides having one or more aryl halo or one or more aromatic nitrogens.

In further important specific aspects, the invention of the '497 application contemplates the provision of certain novel compositions within the last-mentioned class and suitable for use in the practice of one or more of the above-stated methods; and the use of such compositions in the same methods. These compositions include the compound N-(2-diethylamino-ethyl) nicotinamide (which is an N-substituted nicotinamide, hereinafter sometimes referred to as N-NAM), its acid addition salts, acid addition salts of N-(2-diethylamino-ethyl)-4-amino-3-chlorobenzamide (i.e., 3-chloroprocainamide, mentioned above), and mixtures thereof. Preferred acid addition salts are the hydrochlorides, viz., N-(2-diethylaminoethyl) nicotinamide HCl and 3-chloroprocainamide HCl.

Stated broadly, the invention of the '497 application in significant aspects is based on the identification of chemical features that impart properties of radio- and chemosensitization to some members of the group of agents discussed in the above-cited prior art, and embraces the discovery that agents having such properties include a new class of drugs called the N-substituted nicotinamides (e.g. N-NAM).

The invention described in the aforementioned application Ser. No. 08/807,071 ("the '071 application"), in one broad sense, embraces the discovery that at least some benzamides and nicotinamides can selectively induce apoptosis without having any significant effects on necrosis, 1997), and that benzamides and nicotinamides (i.e., other than benzamides with N-pyridinyl substitutions) are useful as anti-inflammatory drugs.

By way of partial explanation of the latter discovery, it may be noted that apoptosis is a normal physiological mechanism contributing to the inflammatory development of several disorders including but not limited to cancer, HIV/AIDS, psoriasis, Alzheimer's disease, Hodgkin's disease, Huntington's chorea, ischemic injury, and many other autoimmune and neurodegenerative diseases (Thompson, Science 267: 1456–1462, 1995); hence, the ability of at least some benzamides and nicotinamides to selectively induce apoptosis without having significant effect on necrosis suggests that the benzamides and nicotinamides may be useful as antiinflammatory drugs.

Also pertinent to an understanding of the foregoing may be the discussions of the molecular biology of inflammation and apoptosis presented in Science 274: 782–789 (Nov. 1, 1996), which set forth that the transcription factor known as nuclear factor kappa B (NF-κB) both inhibits the primary pro-inflammatory cytokine, tumor necrosis factor alpha (TNF-α), and induces apoptotic killing of cells important to the development of new cancer chemotherapeutic strategies. As the benzamides and nicotinamides, particularly the N-substituted analogs, selectively induce apoptosis, then NF-κB inhibition being a known regulator of apoptosis may also inhibit the inflammatory response by likewise inhibiting TNF-α production in inflammatory target cells.

More particularly, the invention of the '071 application embraces the discovery that this is the case, i.e., that both the induction of apoptosis and the inhibition of TNF-α are mediated by the benzamides and nicotinamides giving this class of compounds both anti-cancer and anti-inflammatory properties.

The practice of the invention of the '071 application entails the use of administering to a human or other warm blooded animal: (i) that suffers from an inflammatory disorder such as but not limited to systemic lupus erythromatosis, rheumatoid arthritis, asthma, sepsis, ulcerative colitis, HIV/AIDS, psoriasis, Alzheimer's disease, Hodgkin's disease, Huntington's chorea, ischemic injury, (ii) by an appropriate route such as orally, intravenously, intramuscularly or subcutaneously, (iii) an amount of a benzamide or nicotinamide analog (other than benzamides with N-pyridinyl substitutions) either in a single or repeated dose schedule satisfactory to inhibit TNF-α production in vivo, (iv) that would inhibit the inflammatory response, and (v) that in turn would provide preventive or therapeutic value in controlling health disorders. In another aspect, the invention of the '071 application embraces the discovery that the composition of all benzamide and nicotinamide analogs, other than benzamides that have N-pyridinyl substitutions, are useful in preventing TNF-α production and thus they induce an anti-inflammatory response and have potential preventive or therapeutic value in the clinic. Furthermore, the invention of the '071 application embraces the discovery that benzamides in general and specifically the N-substituted benzamides, other than the pyridinyl-N-substituted benzamides, possess the potent anti-inflammatory properties of inhibiting the production of TNF-α and inducing apoptosis.

Thus, in one sense, the invention of the '071 application contemplates the provision of a method of treating inflammatory disorders comprising administering, to a human or other animal suffering from an inflammatory disorder, an amount of a composition selected from the group consisting of benzamide and nicotinamide analogs and mixtures thereof, other than benzamides with N-pyridinyl substitutions, such amount being effective to inhibit TNF-α production, thereby to inhibit an inflammatory response in the treated human or other animal.

Also in accordance with the invention of the '071 application, in certain advantageous embodiments thereof, the composition comprises, in combination, at least one compound selected from the group consisting of N-substituted benzamides and nicotinamides, other than benzamides with N-pyridinyl substitutions, that can inhibit TNF-α production in the presence of or as a consequence of pro-apoptotic stimuli and at least one compound selected from the group consisting of benzamide and nicotinamide analogs that can inhibit TNF-α in the absence of pro-apoptotic stimuli.

Additionally, the invention of the '071 application contemplates the provision of an anti-inflammatory agent comprising, in combination, at least one compound selected from the group consisting of N-substituted benzamides and nicotinamides, other than benzamides with N-pyridinyl substitutions, that can inhibit TNF-U production in the presence of or as a consequence of pro-apoptotic stimuli and at least one compound selected from the group consisting of benzamide and nicotinamide analogs that can inhibit TNF-α in the absence of pro-apoptotic stimuli.

Specifically, as stated in the '071 application, it is found that those N-substituted benzamides and N-substituted nicotinamides that exhibit the property of radiosensitization (e.g., metoclopramide, 3-chloroprocainamide, and 2-methoxy-N- (2-diethyl-aminoethyl) nicotinamide) can inhibit TNF-α production in the presence of or as a consequence of pro-apoptotic stimuli, while benzamides and nicotinamides other than the N-substituted analogs that exhibit the radiosensitizing property can inhibit TNF-α in the absence of pro-apoptotic stimuli.

SUMMARY OF THE INVENTION

The present invention broadly embraces a new compound, N-acetyl-3-chloroprocainamide (hereinafter sometimes referred to as N-acetyl-3-CPA); its acid addition salts; and uses thereof.

This compound and its acid addition salts are useful agents in the treatment of cancer and inflammation. They can be employed in the methods described in the '497 and '071 applications in place of the antitumor and anti-inflammatory agents (such as metoclopramide and 3-CPA) specifically exemplified therein.

Thus, in a first aspect, the invention contemplates the provision of a composition comprising at least one compound selected from the group consisting of N-acetyl-3-chloroprocainamide and acid addition salts thereof. One such acid addition salt, specifically within the contemplation of the invention, is N-acetyl-3-chloroprocainamide hydrochloride.

Further in accordance with the invention, there may be provided a formulation for administration to a human or other animal comprising at least one compound selected from the group consisting of N-acetyl-3-chloroprocainamide and acid addition salts thereof, and a pharmaceutically acceptable carrier.

In a second aspect, the invention contemplates the provision of methods of inhibiting or killing tumor or cancer cells in a human or other animal, including methods that are procedurally specifically described and exemplified in the '497 application. These include a method consisting essentially of treating the human or other animal with a composition selected from the group consisting of N-acetyl-3-chloroprocainamide, its acid addition salts, and mixtures thereof; and a method of inhibiting or killing tumor or cancer cells in a human or other animal, consisting essentially of treating the human or other animal with radiation or a chemotherapeutic agent together with a composition selected from the group consisting of N-acetyl-3-chloroprocainamide, its acid addition salts, and mixtures thereof, in an amount effective to enhance the cytotoxicity of the radiation or chemotherapeutic agent employed. One exemplary chemotherapeutic agent that may be employed in the latter method is cisplatin.

In yet another aspect, the invention contemplates the provision of a method of treating inflammatory disorders comprising administering, to a human or other animal suffering from an inflammatory disorder, an amount of a composition selected from the group consisting of N-acetyl-3-chloroprocainamide, its acid addition salts, and mixtures thereof, said amount being effective to inhibit TNF-α production, thereby to inhibit an inflammatory response in said human or other animal. Such a method includes methods that are procedurally specifically described and exemplified in the '071 application.

In a broad sense, the invention embraces the use of N-acetyl substituted aryl analogs of N-substituted benzamides and nicotinamides, their acid addition salts, and mixtures thereof, generally, as such anti-cancer and anti-inflammatory agents.

Further features and advantages of the invention will be apparent from the detailed description hereinafter set forth, together with the accompanying drawings.

DETAILED DESCRIPTION

Figure 1:
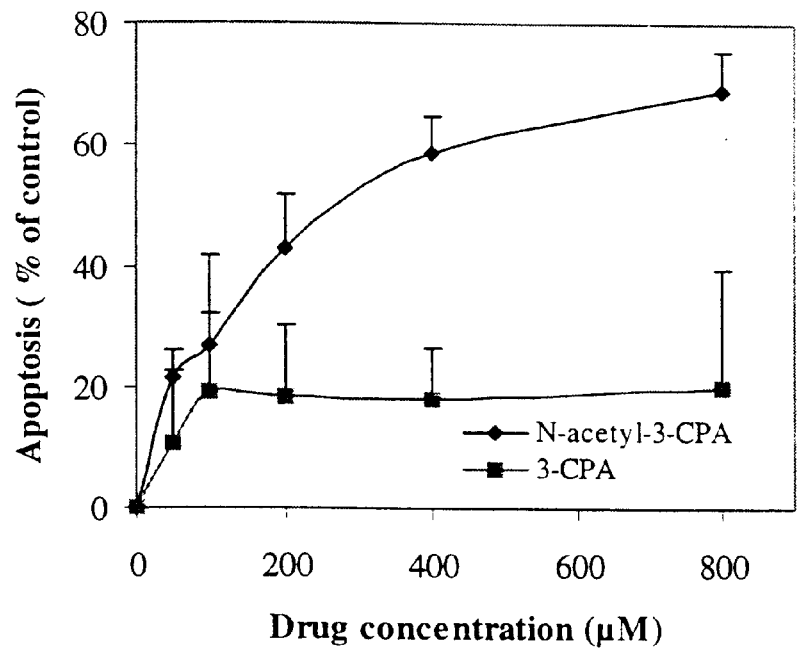
FIG. 1 is a graph showing the relationship between N-acetyl-3-chloroprocainamide dose and induction of apoptosis in HL60 cells. Apoptosis (% of control) was assessed by DNA fragmentation assay and results were expressed as the mean±SD (n>=3).

The '497 application describes in detail a synthesis of 3-chloroprocainamide (free base and hydrochloride). The 3-chloroprocainamide hydrochloride referred to below can be prepared by this synthesis.

N-acetyl-3-chloroprocainamide, a novel compound, is an Nacetyl substituted analog of 3-chloroprocainamide. It and its acid addition salts, e.g. the hydrochloride, have utility as antitumor and anti-inflammatory agents in the types of formulations and methods described in the '497 and '071 applications (for instance, in place of the agents therein specifically exemplified, such as metoclopramide, 3-chloroprocainamide and acid addition salts thereof), to which reference may be made for a detailed description of such formulations and methods. The following description, accordingly, is directed specifically to N-acetyl-3-chloroprocainamide and its acid addition salts, and is to be read in conjunction with the disclosures of the '497 and '071 applications, which as stated above are incorporated herein by reference in their entirety.

N-Acetyl-3-Chloroprocainamide Hydrochloride (1). 3-Chloroprocainamide hydrochloride (3-CPA), 8.0 grams (26.2 mmol, supplied by OXiGENE, Inc.) was placed in an oven dried 100 mL round bottomed flask fitted with a rubber septum, a dry argon feed, and a magnetic stir bar, and 50 mL of acetic anhydride was added (46.2 grams, 453 mmol, Fisher). The flask was then immersed in an oil bath, and the suspension warmed over the course of an hour from room temperature to 100° C. (bath temperature), at which point all of the 3-CPA dissolved to afford a homogeneous clear, water-white solution. The flask was then removed from the oil bath and allowed to cool slowly to room temperature (a large amount of white solid precipitates). Cold (~4° C.) absolute ethanol (10 mL) was then added to the flask and the flask shaken to break up the precipitate. The resulting suspension was filtered and the filter cake washed with two additional 20 mL portions of cold absolute ethanol. The resulting crystals are dried under vacuum to afford 6.7 grams (19.3 mmol, 74%) of the desired N-acetyl-3-chloroprocainamide hydrochloride, which required no additional purification. The ethanol washes can be concentrated and the resulting white solid recrystallized to afford additional pure product (the reaction is essentially quantitative). $^1$H NMR (D$_2$O; J in Hz) δ7.84 (1H, d, J=1.9), 7.70 (1H, d, J=8.5), 7.65 (1H, d of d, J=1.9, 8.5), 3.71 (2H, t, J =6.2), 3.34 (2H, t, J=6.2), 3.25 (4H, q, J=7.3), 2.18 (3H, s), 1.25 (6H, t, J=7.3). HPLC–R$_f$=9.7 minutes (5×250 mm Alltech Altima C-18, solvent A=0.1% aqueous trifluoroacetic acid (TFA); solvent B=0.1% TFA in 9:1 CH$_3$CN:H$_2$O; flow rate=1.0 mL/min, gradient of 10% to 60% B over 30 minutes). reference R$_f$ (3-CPA)=11.85 min.

N-Acetyl-3-Chloroprocainamide Hydrochloride (1)

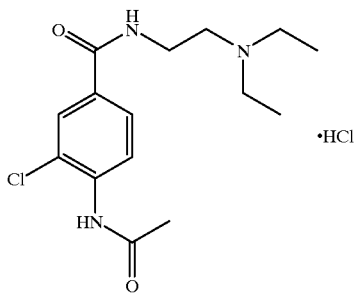

Evaluation of apoptosis by DNA fragmentation. DNA fragmentation by agarose gel electrophoresis HL60 cells (2×106) were incubated with N-acetyl-3-CPA at different concentrations for 24 hr. The cells were then pelleted and suspended in 0.25 ml TE-buffer (10 mM Tris, 1 mM EDTA, pH 8.0) and 0.25 ml lysis buffer (5 mm Tris, 20 mM EDTA, 0.5% Triton X-100, pH 8.0). The samples were spun at 13,000 g for 15 min after 30 min of incubation at 4 (C. The supernatants were transferred to new tubes and 1 ml cold ethanol and 25 (1.5 M NaCl added, and then stored over night in the freezer. The DNA samples obtained by centrifugation and dried in vacuum, were dissoluble resuspended in 30 (1 TE-buffer and digested consecutively by adding 1 (1 RNAse A (50 mg/ml) and 1 (1 proteinase K (25 mg/ml) followed by incubation in a water bath at 37 C for 1 hour. The DNA sample was cast and run in a 1.8% agarose gel. After the addition of 5 (1 sample buffer (0.5% SDS, 0.25% bromophenol blue and 40% sucrose in TE-buffer).

Evaluation of sensitization of cisplatin-induced tumor toxicity by N-acetyl-3-CPA. Male mice were divided into 5 groups with 8 mice in each group when the average tumor volume reached 120 mm$^3$. Group 1 was orally given 250 µl physiological at 0, 24 and 48 hours as placebo control. Group 2 was orally administered N-acetyl-3-CPA at 20 mg/kg in a volume of 250 µl at 0, 24 and 48 hours. Group 3 was orally administered N-acetyl-3-CPA at 40 mg/kg in a volume of 250 µl at 0, 24 and 48 hours. Group 4 was intramuscularly administered cisplatin at 7.5 mg/kg at 0 hour. Group 5 was intramuscularly administered cisplatin at 7.5 mg/kg at 0 hour and orally administered N-acetyl-3-CPA at 40 mg/kg in a volume of 250 µl at 0, 24 and 48 hours.

EXAMPLE

Figure 2:
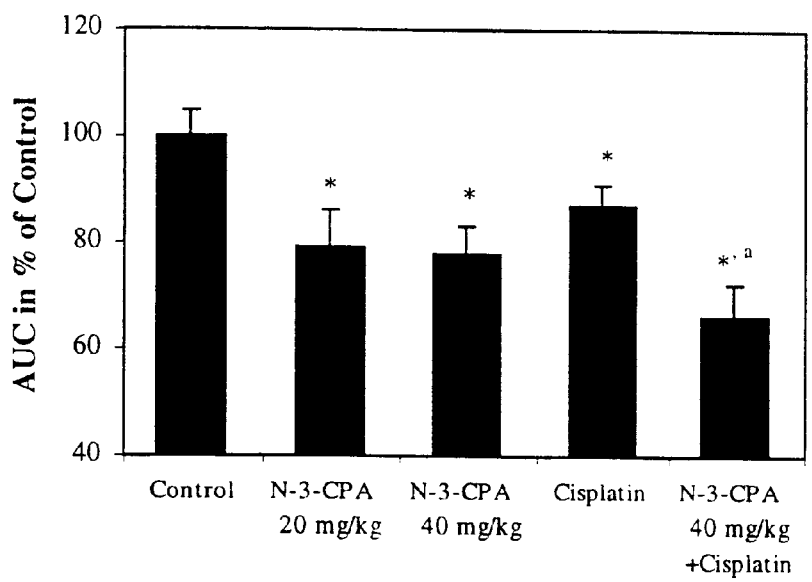
FIG. 2 is a graph showing antitumor activity of N-acetyl-3-chloroprocainamide in scid mice xenografted with a human brain astrocytoma (T24) evaluated by area under tumor growth curve (AUC) in % the control. Animals were treated by oral administration with N-acetyl-3-CPA at 20 or 40 mg/kg×3 (N-acetyl-3-CPA 20, N-acetyl-3-CPA 40), cisplatin at 7.5 mg/kg and in combination with N-acetyl-3-CPA at 40 mg/kg (N-acetyl-3-CPA+cisplatin). Data are mean of 8 animals±SEM. *: p<0.05 vs. the control. a: p<0.05 vs. the cisplatin alone.

This example demonstrates that N-acetyl substituted aryl analogs of N-substituted benzamides and nicotinamides such as N-acetyl 3-chloroprocainamide (N-acetyl 3-CPA) are efficient inducers of apoptosis, and therefore, they are useful agents in the treatment of cancer and inflammation. The data in FIG. 1 show that N-acetyl 3-CPA dose dependently induces apoptosis. Apoptosis in turn is a natural process whereby immunologically competent cells can be modulated during inflammatory responses because of a similar transcriptional control mechanism mediated by NF-kB, or during the cytotoxic responses of tumor cells. Further evidence that N-acetyl benzamides have potential as drugs for the treatment of cancer both as antitumor and radio- or chemo-sensitizing agents can be found in FIG. 2. Here it is demonstrated that the values for area under the tumor growth curves (AUC) compared with controls are reduced in scid mice xenografted with a human glioma and exposed to N-acetyl 3-CPA. Mice treated with N-acetyl-3-CPA at 20 mg/kg showed 81% inhibition of tumor growth compared to controls, and at 40 mg/kg it was 80%. This inhibition was also confirmed when combined with cisplatin as a chemosensitizer, where it retarded tumor growth by 66% which was significantly greater than the effect of cisplatin alone (82% of the control, p<0.05). Taken together these data show that substitutions of an amino group located on the benzamide or nicotinamide ring do not destroy the usefulness of the benzamide and nicotinamide class of drugs as potential anti-inflammatory or antitumor agents.

As described in U.S. Pat. No. 5,561,161, the disclosure of which is also incorporated herein by this reference, it is advantageous to administer formulations of N-substituted benzamides (and their acid addition salts) to humans at a pH of about 5.5 to about 7.0 and/or free of $Na^+$ ions. Formulations of N-acetyl-3-chloroprocainamide and its addition salts (e.g. hydrochloride) can be provided, for administration to humans, at a pH of about 5.5 to about 7.0 and/or free of $Na^+$ ions.

It is to be understood that the invention is not limited to the features and embodiments hereinabove specifically set forth, but may be carried out in other ways without departure from its spirit.

What is claimed is:

1. A composition comprising at least one compound selected from the group consisting of N-acetyl-3-chloroprocainamide and acid addition salts thereof.

2. A composition as defined in claim 1, comprising N-acetyl-3-chloroprocainamide.

3. A composition as defined in claim 1, comprising N-acetyl-3-chloroprocainamide hydrochloride.

4. A formulation for administration to a human or other animal comprising at least one compound selected from the group consisting of N-acetyl-3-chloroprocainamide and acid addition salts thereof, and a pharmaceutically acceptable carrier.

5. A method of inhibiting or killing tumor or cancer cells in a human or other animal, consisting essentially of treating the human or other animal with a composition selected from the group consisting of N-acetyl-3-chloroprocainamide, its acid addition salts, and mixtures thereof.

6. A method of inhibiting or killing tumor or cancer cells in a human or other animal, consisting essentially of treating the human or other animal with radiation or a chemotherapeutic agent together with a composition selected from the group consisting of N-acetyl-3-chloroprocainamide, its acid addition salts, and mixtures thereof, in an amount effective to enhance the cytotoxicity of the radiation or chemotherapeutic agent employed.

7. A method according to claim 6 of inhibiting or killing tumor or cancer cells in a human or other animal, consisting essentially of treating the human or other animal with a chemotherapeutic agent together with a composition selected from the group consisting of N-acetyl-3-chloroprocainamide, its acid addition salts, and mixtures thereof, in an amount effective to enhance the cytotoxicity of the chemotherapeutic agent employed.

8. A method according to claim 7, wherein said chemotherapeutic agent is cisplatin.

9. A method of treating inflammatory disorders comprising administering, to a human or other animal suffering from an inflammatory disorder, an amount of a composition selected from the group consisting of N-acetyl-3-chloroprocainamide, its acid addition salts, and mixtures thereof, said amount being effective to inhibit TNF-α production, thereby to inhibit an inflammatory response in said human or other animal.

* * * * *